United States Patent [19]
Mueller-Glauser et al.

[11] Patent Number: 5,634,879
[45] Date of Patent: Jun. 3, 1997

[54] PROCESS FOR PREPARING A POROUS GRAFT CONTAINING ENDOTHELIAL CELLS

[75] Inventors: Werner Mueller-Glauser; Franz Rieser, both of Wiesendangen; Pedro Bittmann, Zurich; Eric Dardel, Seuzach, all of Switzerland

[73] Assignee: Sulzer Medizinaltechnik, Winterthur, Switzerland

[21] Appl. No.: 56,746

[22] Filed: May 4, 1993

[30] Foreign Application Priority Data

May 11, 1992 [CH] Switzerland ............... 01498/92

[51] Int. Cl.⁶ .................... A61F 2/02; A61F 2/06
[52] U.S. Cl. .................................. 600/36; 623/1
[58] Field of Search .............. 623/1; 435/240.21, 435/240.241, 240.23; 600/36

[56] References Cited

U.S. PATENT DOCUMENTS

| | | | |
|---|---|---|---|
| 5,035,708 | 7/1991 | Alchas et al. | 623/1 |
| 5,171,261 | 12/1992 | Noishiki et al. | 623/1 |
| 5,230,693 | 7/1993 | Williams et al. | 600/36 |

FOREIGN PATENT DOCUMENTS

| | | | |
|---|---|---|---|
| 0248247 | 12/1987 | European Pat. Off. | 623/1 |
| 0399340A1 | 11/1990 | European Pat. Off. | |
| 0444270A1 | 9/1991 | European Pat. Off. | |

*Primary Examiner*—David H. Willse
*Attorney, Agent, or Firm*—Kubovcik & Kubovcik

[57] ABSTRACT

A process for the production of prostheses wherein endogenic tissue material is substantially mechanically comminuted and, if necessary, additionally enzymatically digested to tissue particles, whose sizes fall within very narrow limits. A preshaped carrier material is treated with the resultant suspension. In the case of a porous carrier material the suspension is filtered through the material, whereas with less or non-porous carrier material the suspension is applied to the material surface by centrifuging. Unlike the case of corresponding prior art processes, as a result of this improvement, the process according to the invention can be performed very rapidly, i.e., directly during the operation and in a closed system.

9 Claims, 1 Drawing Sheet

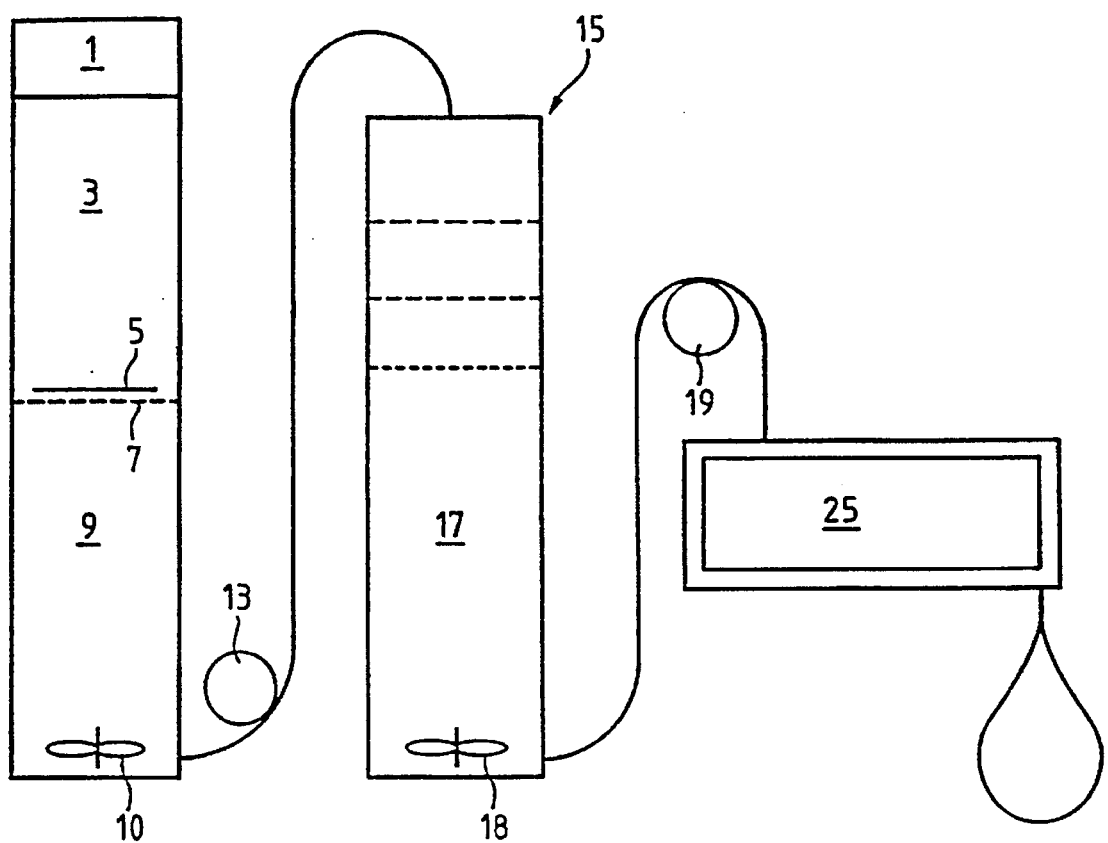

PROCESS FOR PREPARING A POROUS GRAFT CONTAINING ENDOTHELIAL CELLS

BACKGROUND OF THE INVENTION

1. Field of the Invention

The invention relates to a process and an apparatus for producing endoprostheses for an at least partial direct contact with the blood or lymph, such as blood or lymphatic vessel prostheses, cardiac valves, artificial hearts, etc., an endogenic cell-containing suspension being prepared and a preshaped, synthetic carrier material being treated with this suspension. As a result of the implantation of such endoprostheses it is possible to assist the regeneration of parts of the cardiovascular system in humans and animals.

2. Description of the Prior Art

Endoprostheses wholly or partly in direct contact with blood or lymph must fulfil specific requirements, which do not have to be fulfilled in the case of endoprostheses which only have to grow together with the tissue. Natural blood or lymphatic vessels or other blood or lymph-carrying cavities are covered on their inner surfaces with a special cellular layer, namely the endothelium. Between the blood and the endothelial cells a complete matching occurs, which gives the blood or lymph its full and very complex, normal functionality or prevents coagulation. This function has only been moderately fulfilled by endoprostheses introduced in bloodstreams up to now. It can be assumed that despite the most intensive research in this field synthetic materials are not of an optimum nature for long term use and expose the blood or lymph to additional stress, which does not occur in the case of the natural tissue, i.e., the endothelium.

At the latest since 1978 when the words of Herring et al ("A Single-staged Technique for Seeding Vascular Grafts with Autogenous Endothelium", *Surgery* 84:498–504, 1978) were published, it has been known that endogenic endothelial cells, e.g., obtained from veins, form an anticoagulating layer if applied to the inner surface of the vascular prostheses and are exposed to the bloodstream again following implantation.

Because when obtaining endothelial cells from veins it is generally only possible to remove portions having a very limited length of typically 5 to 10 cm, between the removal of the vein portion and the implantation of the coated prosthesis, there must be a stage of proliferating the removed endogenic endothelial cells, which is carried out in a cell culture laboratory and generally lasts one to three weeks. Considerable risks are involved in this intermediate stage. First throughout the time of in vitro culturing an absolute sterility must be ensured, so as to neither endanger the cultured cells, nor subsequently the patient by an infection. In addition, during such a proliferation there are changes to the cells and a so-called dedifferentiation occurs, which is due to the in vitro culture conditions and during which the cells fall back into a less specialized state for which there is no precise correspondence in the body. The question therefore arises to what extent the cells obtained under artificial conditions during a culturing period involving several proliferation stages, although obtained from the patient's body, actually correspond to the endogenic cells with respect to their functions during prosthesis implantation.

Jarrell et al ("Use of Freshly Isolated Capillary Endothelial Cells for the 100:392–399, 1986), Schmidt et al ("Microvascular Endothelial Cell Seeding of Small Diameter Dacron Vascular Grafts", *J. Invest Surg.*, 1:35–44, 1988), Pearce et al ("Successful Endothelial Seeding with Omentally Derived Microvascular Endothelial Cells", *J. Vasc. Surg.*, 5:203–210, 1987) and other authors have shown by means of animal experiments that endothelial cells isolated from microvessels adapt and can take over the function of arterial endothelial cells, if seeded in arterial prostheses, in which, e.g., the physiological blood flow rate is much higher than in the microvascular part of the vascular network from which the cells were isolated. It is, therefore, known that in vascular prostheses, which are seeded with microvascular endothelial cells, e.g., in the case of dogs, a functional, anticoagulating lining is formed. The microvascular endothelial cells can, e.g., be obtained from adipose tissue, e.g., by removing part of the omentum or a limited quantity of subcutaneous adipose tissue.

It has been found in practice that per gram of removed adipose tissue it is possible to obtain approximately 100,000 and occasionally even 1,000,000 vital microvascular cells. If it is assumed that a prosthesis with an internal diameter of 6 mm and a length of 100 cm has a surface area of approximately 200 $cm^2$ and that the supply of the surface with approximately 100,000 cells per $cm^2$ is sufficient in order to regenerate the athrombogenic layer by implantation, a simple calculation shows that with the removal of max 200 g of tissue, sufficient cellular material can be obtained to carry out the coating of a complete bypass from the groin down to the foot. This means that the above-described, in vitro proliferation for the production of the number of endothelial cells necessary for prosthesis coating can be obviated, i.e., macrovascular, endogenic endothelial cells can be obtained in quantities such that the prosthesis can be completed immediately following tissue removal, provided that a sufficiently rapid process is available for isolating the cells.

Whereas in the case of the method with in vitro proliferation according to Mansfield et al ("Preventing Thrombus on Artificial Surfaces: True Endothelial Cell Linings", *Trans. Am. Soc. Artif. Intern. Organs.*, 21:264–272, 1975) and all subsequent authors one to three or more weeks must elapse (as a function of the culture system efficiency) between the removal of parts of larger vessels (arteries, veins) for obtaining vascular, endogenic endothelial cells from the patient and prostheses implantation, when using microvascular endothelial cells according to Schmidt et al (*J. Invest. Surg.*, 1:35–44, 1988) this period of time can be reduced to three hours, because the cellular proliferation stage is omitted. However, the latter process has also not entered surgical routine, particularly because it is not sufficiently fast. In a coronary bypass operation use is still advantageously made of the patient's own vessels for bridging vasoconstrictions. The surgeon expects a period of about one hour between the time at which the start of removal of veins from the leg takes place and the time when the prepared vein is ready for sewing into the cardiac region.

The known endoprosthesis production process is as follows. In a first process step, from the preferably subcutaneous adipose tissue of a patient, which contains in addition to the microvascular cells a large number of other cells and non-cellular tissue components, microvascular cells are isolated and in a further process step are applied to specific surface parts of a preshaped, artificial carrier. It has been found that following the implantation of prostheses produced in this way during a period of weeks to months a tissue evolves on the surface parts permanently in contact with the blood which is similar to the endothelium of natural vessels and is located on a tissue layer, which is also similar to the natural artery wall (Schmidt et al, *J. Invest. Surg.*, 1:35–44, 1988). Therefore, these tissues which, e.g., form on the inside of vascular prostheses are referred to as neoarteries. Like the natural artery, the neoartery is completely covered with athrombogenic endothelial cells, so that blood does not coagulate in the prosthesis and can function fully and in an undisturbed manner.

The first process step consists of the isolation of the microvascular cells desired for incorporation as a result of the mechanical comminution of the tissue removed from the patient, followed by enzymatic digestion of the comminuted tissue with a suitable enzyme and the separation of all undesired constituents from the suspension prepared by digestion for the isolation and concentration of the microvascular cells.

In the works of Schmidt et al (*J. Invest. Surg.*, 1:35–44, 1988) and Jarrell et al (*Surgery*, 100:392–399, 1986), for said isolation, following enzymatic digestion, there is a stage of cell purification and/or cell sorting. The cell suspension obtained by digestion is separated into the different cell types in one or more centrifuging stages and in certain circumstances even with the aid of a so-called density gradient, and is freed from non-cellular tissue components. As a result of centrifuging, e.g., the specifically lighter, fat-containing adipocytes can be separated from the endothelial cells, which have a higher specific gravity.

For the coating of the prosthesis with the isolated cells they are incorporated into the corresponding prosthesis surface either by the filtration of the suspension through a porous prosthesis or by centrifuging in a rapidly rotating prosthesis (Swiss Patent Application No. 2004/90-3 of the same coapplicant, applied for on 15.6.1990).

The problem of the present invention is to so improve the above-described process for producing an endoprosthesis by producing and endogenic cell-containing suspension and subsequently treating a preshaped, artificial carrier material with said suspension in such a way that it is suitable for use in the operating theatre. The complete process for producing the suspension and the subsequent treatment of the prosthesis with the suspension should take up no more time than the surgical preparations for prosthesis implantation. Thus, using the process according to the invention it must be possible to, e.g., implant an endoprosthesis with incorporated endogenic, microvascular endothelial cells, the endogenic cells used being removed during the same operation, e.g., in the form of subcutaneous adipose tissue. Thus, the known process must be improved in such a way that one hour is sufficient for the preparation of the suspension and the subsequent treatment of the prosthesis with the suspension and that the prosthesis produced according to the process of the invention assists the regeneration of the endothelium to at least the same extent as prostheses produced according to the prior art processes. The technical problem is to prepare the transplantation material in a minimum number of simple process steps with a minimum number of manipulations, but despite this ensuring that the transplanted cells are able to completely fulfil in an optimum manner their allocated function following transplantation.

SUMMARY OF THE INVENTION

The problem of improving the above-described, known process is solved by the process according to the present invention.

The improvements according to the invention are essentially based on the following findings:

Even if the suspension is prepared from a tissue which, apart from the cells desired for incorporation, has large amounts of other cells and non-cellular tissue components, it is not necessary to isolate the desired cells from the mixture. It is sufficient to adequately finely comminute the tissue and suspend the same and immediately treat the carrier therewith. Thus, the carrier is not treated with a suspension of, e.g., microvascular cells, but with a suspension of tissue particles, e.g. of tissue particles prepared from adipose tissue removed from the patient.

The tissue particles are prepared by the mechanical comminution of the tissue material removed and, if necessary, by a following enzymatic digestion. As a result of a corresponding mechanical comminution it is ensured that the resulting tissue particles have a narrow size distribution. Therefore, the action during enzymatic degradation is more regular and the product more homogeneous. However, if in spite of this the size distribution of the tissue particles does not meet requirements, e.g., because there are excessively large particles for the treatment of very small internal diameter vascular prostheses, prior to the treatment oversized particles can be removed by filtering the suspension.

In addition, a large part of the fatty component can be separated from the suspension by allowing the suspension to sediment and separating the phases.

The byproducts resulting from the enzymatic digestion need not necessarily be removed from the suspension before the carrier is treated therewith. If necessary, following the incorporation of the tissue particles, the carrier can be rinsed with a rinsing solution.

In the process according to the invention all the partial steps are precisely controlled and matched in an optimum manner to one another. This is made possible as a result of a newly discovered and unexpected effect, on the basis of which the entire process can be performed very quickly, simply and in a closed system. These principles of the invention and the advantages resulting therefrom will now be described in detail.

It has surprising been found that there is no need to separate by centrifuging the suspension obtained by digestion. If necessary, centrifuging can be replaced by merely allowing the suspension to settle. The purification obtained by allowing the suspension to sediment or settle and separation of the heavier layer containing the cells to be transplanted from the lighter, fat-containing layer is adequate when treating adipose tissues for a subsequent carrier treatment. Following the application of the suspension to the prosthesis inner surface, in the case of porous prostheses further oily-fatty constituents can be washed out by a rinsing process through the prosthesis wall.

Lipid determinations have shown that only insignificantly higher fat quantities per cm of prosthesis length are left behind if the centrifugal stage is replaced by direct rinsing on the prosthesis. In accordance with this, experiments using the canine model (implantation in A. carotis) have provided proof that cellular suspensions containing further cell fractions and which do not belong to the natural cell population at the implantation point, lead to no observable change in the healing process and in the formation of the neoartery in the prosthesis. In particular, no hypertrophy of the tissue could be measured and scanning electron microscopic examinations of the inner prosthesis surface revealed a closed endothelial cell layer.

Bearing in mind these two surprising findings, there is in particular no need for a complicated separation or isolation based on cell types.

It is also possible to obviate the need for the purification of the cellular suspension for obtaining the cells required for tissue regeneration, so that the cellular suspension obtained from the digestion stage can be directly used for coating the prosthesis. This more particularly applies in the case of porous prostheses. It has surprisingly been found in the canine model, that a porous prosthesis can be used as a filter, which retains the cells and cell unions, whereas the dissolved constituents and in particular also the enzymes for tissue digestion, e.g., collagenase, are washed out. Thus, a purification of the cells and cell unions adequate for implantation is obtained. A purification stage by centrifuging is here replaced by purification by filtration on the prosthesis. This simplification (no centrifuging) makes it possible to fulfil in a surprisingly simple manner one of the main requirements, namely the sterility requirement. In addition, the process is continuous and therefore can be automated, which according to the prior art was only possible with a complicated continuous centrifuging process.

Surprisingly, the canine model has also revealed that there is no need to separate the fatty phase following enzymatic tissue digestion. This means that the process can be significantly simplified, in that immediately following tissue digestion the entire suspension can be transferred by means of a pump and via a stage filter (for separating excessively large tissue particles) directly to the prosthesis, which retains the cells and cell unions, whereas all the dissolved constituents can very efficiently and simply be washed out by a following rinsing stage.

For prosthesis coating it is necessary to have tissue particles, which contain the maximum number of vital cells and whose size is such that they can be subsequently incorporated into the microporous structure of the carrier material without excessively projecting into the internal diameter of the prosthesis, so as to possibly be torn away on releasing the bloodstream, which can lead to microembolisms. According to the invention, tissue particles with a very uniform size and a large number of vital cells can be obtained in that the mechanical comminution stage and the enzymatic digestion stage are precisely matched to one another. Of the various known enzymes for digestion, e.g. pancreatin, dispase, trypsin, etc., collagenase has proved particularly suitable in in vitro tests. As a result of its specific action collagenase contributes to the dissolving of individual cells from the tissue, together with small cell unions, without damaging the vitality of the cells. If collagenase had a 100% specificity for the collagen of the extracellular matrix, it might bring about tissue digestion, without damaging the cells or their surface. This would be an ideal picture, because it has been found that cells exposed for a long period to the action of proteolytic enzymes, e.g. collagenases, suffer damage on their surface receptors and can entirely lose their vitality.

Thus, the action time of the enzyme must be sufficiently long to split up the tissue into sufficiently small particles, the necessary time being significantly dependent on the size of the available particles. However, it must not be too long, so as not to unnecessarily reduce the vitality of the cells dissolved out. Since, as a result of this, there are no common, optimum digestion parameters for particles of different sizes, a corresponding mechanical comminution of the tissue is required to ensure that the tissue particles to be digested are as small as possible and preferably of the same size.

According to the invention, enzymatic digestion is preceded by a cell-protecting, mechanical comminution in such a way that tissue particles are obtained, which are as far as possible of the same size. Comminution processes are cell-protecting if the tissue is cut and not squeezed or crushed. According to the invention this is brought about by the treatment of the tissue with a large number of very sharp blades moving in a coordinated manner. A narrow, precisely defined size distribution of the tissue particles to be digested makes it possible to determine a clearly defined, optimized collagenase action time.

If mechanical comminution leads to tissue particles with dimensions of approximately 0.02 to 1.0 mm and preferably 0.05 to 0.5 mm, for the comminution of, e.g., a vein or granulation tissue (tissue in sponge matrix gemäss Bishop et al. *Humm. Immunol.* 28:128–133, 1990) for the treatment of a vascular prosthesis there is no need for enzymatic digestion.

As the process for the production of vascular prostheses is a tissue transplant, in which vital cell-containing tissue particles are so implanted on a carrier that the corresponding organ, in this case, e.g., a vascular prosthesis or a cardiac valve, can be regenerated in accordance with the given structure shape, it is conceivable that this tissue transplantation principle can also be used for other organs, e.g., the pancreas or spleen, if the process is correspondingly adapted to the necessary cell types and tissue. If it is possible to cut the tissue in a clearly defined manner, so that the particles containing the extracellular matrix and the resulting cells allow the migration of the cells onto the prosthesis structure provided, there is no need for the enzymatic digestion stage, e.g., in that a vein is comminuted in such a way that the resulting tissue particles can be directly applied to a small diameter, i.e. <8 mm ID prosthesis, without obliterating the prosthesis internal diameter. In addition, the tissue particles retain their capacity to initiate the formation of the neoartery, e.g., as a result of a biological process in the body, such as occurs when a neoartery is formed in a prosthesis with microvascular cells from adipose tissue.

EMBODIMENT

An embodiment of the process according to the invention will now be discussed in detail using the basis of an endothelialized vascular prosthesis. The performance of the process involves:

1. the preparation of a suspension of tissue particles from an endogenic tissue material,
2. an optional separation of excessively large tissue particles and/or a considerable proportion of the fatty constituents,
3. an optional intermediate storage of the suspension,
4. the treatment of the preshaped artificial carrier with the suspension,
5. an optional prosthesis rinsing,
6. an optional prosthesis treatment for obtaining the moisture necessary for the implanted cells, and;
7. an optional intermediate storage of the prosthesis produced.

Stages 1 and 4 are necessary, whereas the remaining stages may or may not be used, as a function of the prosthesis type and the performance of the operation.

The removed tissue, e.g., omentum or granulation tissue (tissue in sponge matrix gemäss Bishop et al., "Vascular Endothelial Differentiation in Sponge Matrix Allografts, Hum. Immunol., 28:128–133, 1990) or some other vascular tissue is, in order to keep the traumatization of the cells as limited as possible, very carefully mechanically comminuted, in that it is treated with a large number of very sharp blades moving in a coordinated manner. The aim is to obtain a maximum percentage of vital cells, accompanied by a simultaneously high, absolute cell yield. Despite these requirements comminution must take place in a relatively short time, e.g., 1 to 3 minutes/100 g of tissue mass.

The size of the tissue particles which are mechanically comminuted, is limited by the size of the comminutor to be used and typical sizes of parts have dimensions of 3×3×2 or 5×5×2 cm or expressed in weight, 20 to approximately 50 g. These parts must be comminuted to 0.5 to 4 mm, preferably 0.5 to 2 mm in disk, rod or cube form. In the case of tissue cubes of 3×3×3 mm to 4×5×5 mm, this corresponds to a weight of approximately 0.01 to 0.1 g.

The mechanically comminuted tissue is then enzymatically digested, e.g., with collagenase, in order to at least partly free the cells from the connective tissue and consequently further comminute the tissue particles. The collagen and elastic components of the connective tissue are so degraded that the cells are freed, but damaged to the minimum possible extent (minimum decomposition of cell surface constituents). Enzymatic degradation must also take place very rapidly, but carefully and this is controlled by means of the temperature and the enzyme concentration. A movement of the mixture brings about a thorough mixing of the phases, which additionally accelerates degradation.

Various such procedures for the processing of living cells are known and can be correspondingly used. It has surprisingly been found that stirring with a magnetic stirrer is more efficient than shaking the complete reaction vessel. Suitable as magnetic stirring rods are bodies not having sharp edges, e.g., rounded rods, because this prevents any winding up of the tissue. The stirrer is freely suspended or has only a minimum bottom contact, which also prevents a grinding of the suspended cellular material.

It is, e.g., possible to use collagenase for digestion and a recommended concentration is approximately 400 to 20,000 Mandl-U/ml, typically 750 to 3,000 U/ml, while the temperature is at least 37° C., but does not exceed 40° C. and is preferably 37° to 38° C., while the tissue to enzyme solution volume ratio is 1:1 to 1:2.

Following digestion the suspension can be separated for a partial purification. This part of the process must also be rapidly performed, because the material involved has a relatively high metabolic activity at the processing temperatures, unlike in the case of the processing of cooled tissue materials, while for medical reasons a rapidly performable process is sought.

A purification of the suspension with the aim of achieving a quantitative separation of the enzymes used or the separation of other than endothelial cells is not necessary. It has been found that no disadvantages such as, e.g., increased hypertrophy of the new tissue layer, occur if this purification is omitted or greatly simplified, i.e., performed with only a partial purification result. Thus, there are no known disadvantages if, e.g. the mixture of all the cells isolated from the adipose tissue is used for transplantation in place of a pure endothelial cell suspension.

A partial separation of the suspension for removing excessively large particles or part of the fat-containing constituents can prove advantageous. This can be carried out either using the specific gravity (allowing the suspension to sediment and separating the lighter phase) and/or the size of the aggregates (filtration). The size-based separation is in particular important when using small internal diameter prostheses, so as to prevent any constriction of the internal diameter by excessively large, transplanted particles. However, a size-based separation is also advantageous with large internal diameter prostheses, because for large particles applied there is a significant risk of them being removed from the surface again and consequently leading to microclots in the capillary system. The specific gravity-based separation is advantageous in other applications. Both separating or isolating methods will be briefly discussed below.

Firstly, the gravity-based separation (allowing to sediment and separating the layers): in the case of adipose tissue the particles of the suspension having a relatively large fat proportion float relatively rapidly upwards. Contrary to prevailing opinion there is no need for forced sedimentation by centrifuging and instead sedimentation in the gravitational field is adequate. This leads to the advantage that the sedimentation can be performed in a closed, stationary system.

Sedimentation can be accelerated, e.g., by an appropriate choice of the depth of the sedimentation vessel, by diluting the suspension at the end of enzymatic digestion and/or by other suitable measures. For example, the suspension to be sedimented is diluted with a buffer solution to 1.5 to 10 times and preferably 1.5 to 2 times the volume, e.g., 300 g of tissue+300 ml of enzyme solution=digestion suspension, which can be topped up to 1000 ml for sedimentation corresponding to a 1.67 times dilution. In a 10 cm diameter, 15 cm high cylindrical vessel sedimentation for such volumes lasts 1 to 15 and preferably 3 to 10 minutes. After this time there is a clear boundary between the aqueous and the oily phase. Sedimentation can be assisted by very slow stirring with a magnetic stirrer, because as a result lighter constituents enclosed in the sediment are freed and because, particularly in the case of dense suspensions (collagenase:tissue=1:1), the separation of the tissue particles on the basis of their specific gravity is assisted by the additional, slight movement.

Sedimentation and separation of the resulting layers is preferably performed immediately following enzymatic digestion, preferably in the same vessel and at 20° to 40° C., preferably 30° to 37° C., for adipose tissue.

For vascular prostheses coating a separation of excessively large particles is advantageous. Thus, e.g., in the case of vascular prostheses with an internal diameter of 4 mm, it is necessary to exclude those particles having a diameter larger than 0.4 mm and whose length exceeds 1 mm. For this purpose it is necessary to use sieves or screens with a screen aperture of 0.2 to 1 preferably 0.2 to 0.4 mm. In order to improve the cell yield and prevent clogging, in the case of larger material quantities (as from 50 g of tissue) multistage screens are advantageous. For up to 300 g of tissue, e.g. three stages, are used the screen diameter being 4 to 6 mm and the spacing between two screens being 2 to 6 mm. The screen aperture is, e.g., selected as follows: approx. 2 mm for the first, approx. 0.8 mm for the second and approx. 0.25 mm for the third screen. This ensures that the entire mass of the fraction left behind does not increasingly load a single screen layer, so that an increasing flow resistance would be formed and in particular the screen effectiveness would be drastically modified, so that with increasing loading the size of the particles passing through decreases, leading to considerable cellular material losses. However, in the case of multistage screens, the total number and screen aperture of the screens used are correspondingly distributed and the flow resistance and screening effect are influenced to a much lesser extent.

The screens are preferably vertically superimposed, so that filtration can be performed by gravity, which leads to a more uniform screen charging and therefore permits a better defined filtration. In the case of such an arrangement less equipment is required, which is also advantageous with respect to the strict sterility requirements.

However, it is also possible to carry out filtration by means of pump transport, in which essentially the same criteria must be respected. Pump transport has in particular the advantage that filtration counter to gravity can be carried out, which permits an air bubble-free liquid transport in a simple manner, which is important for the following carrier material treatment.

The pumps are constituted by flow inducers, preferably those with two roller heads. It has surprisingly been found that this only leads to insignificant vital cell losses. However, the use of such pumps makes it possible in a simple manner to bring about a controlled process in a closed system, which is clinically significant with regards to sterility and is also important for the time control performance of the process.

The combination of specific gravity-based cell purification and size-based purification is advantageous if both fat and also other particles over a given size must be excluded, e.g., for small internal diameter vascular prostheses.

The endothelial cells for producing the prostheses mainly occur in the aqueous phase (specific gravity-based separation). The aqueous phase is preferably separated from the oily-fatty phase in that the aqueous phase is removed through the opening at or close to the bottom of the vessel for sedimentation, so that the oily-fatty phase is left behind in the digestion and/or sedimentation vessel.

Dissolved components of the suspension, such as collagenase, which are used for the enzymatic degradation, and liquid components, such as oily fat from the tissue, particularly if only a size-based separation is to be performed, are subsequently removed during or after carrier material treatment.

For alternative uses of the suspension, e.g., for cell extraction for biochemical and diagnostic examinations, it is possible to incorporate conventional centrifuging processes in order to obtain a correspondingly higher cell purity, adipocytes being taken from the oily-fatty phase and endothelial and mesenchymal cells from the sediment.

In order to satisfy the high process sterility requirements, throughout the process, preferably including the application to the carrier material, the suspension must be kept in a closed system, which also contains the carrier. This is made possible, e.g., by hose connections between the digestion vessel and the coating module, with which is performed the incorporation of the cellular material in the surface of the carrier material (in the case of vascular prostheses, e.g., on the inner surface). Liquid transport can take place by means of gravity (different levels during the arrangement of the equipment) or by means of flow inducers, roller pumps or other displacement pumps, in which the suspension only comes into contact with disposable parts. In the following example for liquid delivery for the application of the cellular material to the prosthesis material use was made of a Watson pump with two rollers having a silicone hose with a diameter of approximately 8 mm and without slip. It has been found that the number of vital cells in the suspension is not significantly reduced, even after pumping five times.

As a function of the particular requirements, two methods can be used for incorporating the cellular material. If the carrier material is porous, use is made of the filtration method, whereas if the prosthesis material is not or is inadequately porous or permeable or if for some reason the filtration method cannot be used, then a rotation method is used, in which the cellular material is applied by means of acceleration (centrifuging) to the prosthesis material surface (Swiss patent application 2004/90-3 of the present Applicant).

The advantage of filtration of the cell suspension through a porous material is that two stages can be performed in a single operation, namely the incorporation of the tissue particles into the prosthesis surface and the washing out of dissolved substances, such as collagenase, and/or liquid phases of the suspension, such as oily fat. Thus, the cellular material is subsequently purified in the same operation (second partial purification).

Importance is attached to the degree of porosity of the prosthesis material or the prosthesis and it is, e.g., determined by means of the water permeability (in this case measured by the Wesolewski method). Higher density prostheses (less than 100 ml water passage/$cm^2$/minute) during the application of the cellular material undergo a different treatment than prostheses with a lower density (over 100 ml/$cm^2$/min). At least during the initial application phase, both materials allow liquid to enter and pass through the material. If subsequently the cell deposition on the prosthesis surface (in this case the tube inner wall) is investigated, it is found that most cells are located close to the inner surface, which is desirable. For example with a wall thickness of 0.2 mm and an approximately uniform Dacron fibril distribution, multicell aggregates are mainly located in the top 5 μm, whereas single cells occur in decreasing numbers to a depth of approximately 100 μm. With larger pores they are mainly filled with correspondingly large aggregates.

Thus, the prosthesis surface roughness makes difficult or almost impossible a floating of cells which have been deposited on or close to the surface.

Flow experiments with prostheses coated in this way, i.e., flow in the longitudinal direction with physiological saline solution with speeds as in peripheral arteries, have revealed in a surprising manner that immediately following filtration in the case of physiological bloodstream speeds virtually no cells are washed out, whereas the biologically active adhesion to smooth surfaces is only approximately 60% concluded after 60 minutes (Jarrell-Radomski et al, "Immediate Vascular Graft Monolayers using Microvessel Endothelial Cells", in: *Endothelial Seeding in Vascular Surgery*, edited by Herring, M. and Clover, J. L., Grune & Stratton Inc. 1987, p 37–55).

In order to achieve an adequately deep deposition of the cells, for a denser (finer pore) prosthesis material more pressure is required for application purposes than with more loosely packed material. However, with such a material the flow quantity or delivery must be adequate in order to compensate the rapid liquid reduction during application. In both cases, apart from capillary effects, the pressure gradient must be adjusted normal to the coated surface.

In a rotation method (Swiss application 20004/90-3 of the present Applicant), suitability more particularly exists with very dense prostheses, which do not have a porosity usable for the filtration method.

In order to reduce the risk of embolisms as a result of the detachment of applied cells and cell unions, as well as other small tissue particles, the vascular prosthesis, following rinsing through the vessel wall (radial rinsing) can be rinsed through the prosthesis internal diameter (axial rinsing). For this purpose, e.g., 200 to 400 ml of physiological solution per minute is pumped axially through the prosthesis at an approximately physiological speed (blood speed at the implantation point). Following cell application by filtration very few cells and very little other tissue material can be washed out, which demonstrates the microembolism safety of the process.

In order to maintain the cell vitality of the prostheses treated with the cellular material up to the time of application, they can be specially protected as the final stage of the process up to wound closure. The cellular layer of the preprepared prosthesis surface is in this way more particularly protected against drying out.

The presently discussed process for the production of auto-transplants according to the invention is usable for transplants in both human and veterinary medicine. Unlike the case of conventional transplants, in which organs or parts thereof are transplanted, here cells and/or cell unions are transplanted onto a biocompatible carrier and are necessary so that following the insertion of the prosthesis in the body there can be a regeneration of a corresponding organ, e.g., a neoartery.

Relative to the drawing, a closed apparatus for performing the process will now be described. All the apparatus components are in part commercially available. The combination of these components in accordance with the presently described, novel and biologically very active process offers an apparatus for producing prostheses according to the present invention. The apparatus can be designed in such a way that it can also be used in the operating theater and permits the production of prostheses according to the invention in situ.

The drawing shows in diagramatically simplified manner a completely sealable apparatus, where the entire process can be performed in a closed vessel and hose system. It can easily be placed on a movable frame and is in this way available in a mobile manner for use, e.g., in the laboratory or operating theater. The closed nature naturally does not exclude the supplies of tissue to be processed, reagents and solutions. However the closed nature is intended to show how the strict sterility requirements can be respected.

A first unit incorporates the equipment for mechanical comminution, a drive 1, a conveying section 3, which is directed at the knife/perforated plate pair 5, 7, whilst for the digestion of the tissue material for releasing the cells there is a digestion cell 9 with a stirrer 10 for assisting digestion and a first sedimentation. The equipment can be connected in such a way that the comminuted tissue mass drops from the perforated plate into the digestion vessel. At the end of the digestion, sedimentation can also take place in this vessel for separating the oily-fatty phase. For this purpose, at the start of sedimentation, the vessel can be further filled with buffer in order to assist separation. Moreover, e.g., using a magnetic stirrer, a slight movement of 0.1 to 1 U/sec can be produced. The suspension obtained in the first unit is transferred by a conveying means 13 into a second unit, which comprises a filter part 15 and a collecting vessel 17. During delivery into the vessel 17, a slight flow is also produced in the vessel 9. The filter part is here a multistage filter for extracting particles of a specific size collected as a suspension in the collecting vessel. Thus, the sedimentation tendency of the suspension is very limited and is removed by a second magnetic stirrer 18 in the vessel 17. A further conveying means 19 transfers the now ready, homogeneous suspension into the third unit 25 for prosthesis coating. This unit preferably comprises a glove box, in which are housed the equipment necessary for coating purposes and the untreated prostheses are already ready for coating. The dry prosthesis is coated in the box 25 with physiological solution, immediately prior to the application of the cells to the prosthesis. Application/coating can take place either manually, or mechanically. If desired, the finished prostheses can be additionally provided with a protection against drying out and, adequately packed, removed by means of a lock from the sterile interior of the coating box and reliably transferred to the sterile operating table with the aid of further special equipment. As a function of the size and complexity of the overall equipment, it can be equipped for the serial production of prostheses or for the ad hoc production of individual prostheses in the operating theatre.

Without a vessel 17, the filter 15 can be placed between the vessel 9 and the coating unit, in such a way that the suspension is transferred directly from the filter to the prosthesis, without any intermediate storage.

We claim:

1. A process for preparing a graft of a synthetic porous material, said graft containing endothelial cells and useful for human surgery comprising:

(a) finely mechanically comminuting endogenic tissue containing non-cellular tissue components to provide tissue particles having a weight in the range of 0.01 to 0.1 g;

(b) digesting the comminuted tissue in a solution containing an enzyme to partly remove non-cellular tissue components from cellular tissue components;

(c) filtering the digested solution to remove particles that cause a risk to the graft or to the vascular system of a patient;

(d) filtering the solution obtained in (c) through said synthetic porous graft whereby particles contained in the solution are retained within pores of the graft; and (e) rinsing the treated graft by passing a saline solution through the graft.

2. Process according to claim 1, wherein the mechanical comminution is performed by a plurality of sharp blades moving in coordinated manner.

3. Process according to claim 1, wherein filtering in step (d) is conducted by the use of gravity or by centrifugal force produced by rotating the porous graft.

4. Process according to claim 1 or 3, wherein in step (e) the saline solution is pressed from the graft surface together with the incorporated particles through the graft material.

5. Process according to claim 1, wherein for the purification of the incorporated tissue particles and for removing inadequately fixed tissue particles, the porous graft is treated with the saline solution parallel to the surface of the graft.

6. Process according to claim 1, wherein the porous graft is a textile graft.

7. Process according to claim 1, wherein the porous graft is a vascular graft.

8. Process according to claim 1, wherein the porous graft is a cardiac valve.

9. Process according to claim 1, wherein the endogenic tissue is at least one of omentum and subcutaneous adipose tissue.

* * * * *